United States Patent [19]

Coye

[11] Patent Number: 4,976,816
[45] Date of Patent: Dec. 11, 1990

[54] LATEX CONTAINER WITH INTEGRAL HOLDING STRAPS, AND METHOD AND APPARATUS FOR MAKING SAME

[76] Inventor: Peter Coye, 777 W. 7th St., Claremont, Calif. 91711

[21] Appl. No.: 221,112

[22] Filed: Jul. 19, 1988

[51] Int. Cl.$^5$ .................. B32B 35/00; B32B 31/04
[52] U.S. Cl. .................. 156/537; 156/245; 156/292; 269/37; 425/269; 425/500
[58] Field of Search ............ 156/245, 292, 537, 538; 383/21–24, 901; 425/813, DIG. 27, 89, 500, 501, 269, 275; 269/37, 45; 29/774, 281.4, 281.5; 493/226

[56] References Cited

U.S. PATENT DOCUMENTS

| | | | |
|---|---|---|---|
| 1,058,447 | 4/1913 | Mahoney | 156/245 |
| 2,291,786 | 8/1942 | Beal | 156/292 X |
| 2,742,064 | 4/1956 | Quist | 269/45 X |
| 2,810,928 | 10/1957 | Raiche | 425/269 |
| 3,818,572 | 6/1974 | Burrell | 29/774 |

*Primary Examiner*—Michael Wityshyn
*Attorney, Agent, or Firm*—Ashen Golant

[57] ABSTRACT

A method and apparatus for integrally bonding two latex surfaces is disclosed, together with a latex bag having integral loops and/or holding straps which is made by the process. Briefly, a first curing latex surface such as a strip of curing latex, is held against a second curing latex surface such as the curing surface of the bag, so that the two surfaces form an integral bond. Preferably, a few drops of latex are added to the interfacing area prior to bringing the two surfaces into contact.

5 Claims, 2 Drawing Sheets

LATEX CONTAINER WITH INTEGRAL HOLDING STRAPS, AND METHOD AND APPARATUS FOR MAKING SAME

BACKGROUND OF THE INVENTION

This invention relates to a method and apparatus for forming an integral bond between two latex surfaces so as to form, for example, an attachment loop which is integral with the surface of a latex container. This invention further relates to receptacles attached to the human body to receive discharges therefrom and, more particularly, to receptacles of this type which include or utilize encircling belts or harnesses to hold the receptacle against the body.

The need for latex rubber receptacles, or bags is particularly well known in the medical field. For example, people suffering from urinary incontinence in conjunction with an external catheter, and people who have undergone colostomies, ureterostomies, and other surgical procedures carry a latex bag under their clothing to collect draining body fluids. In general, latex has been considered a superior bag material over plastic, due to its combination of strength, durability and flexibility.

Generally, drainage bags must be secured to the user's body, and accordingly include a provision for capturing a holding strap which encircles the user's waist, thigh, or other body member. The holding straps have typically been glued to the latex bag and, with the passage of time, have been known to separate from the bag causing the product to fail with occasional embarrassment to the user.

Many attempts have been made in the past to minimize the incidence of strap-separation. In some cases, wherein the straps are glued to the latex, separation has been caused by the inability of the glue to accommodate the relatively greater flexibility, stretchability, and resiliency of the latex without destruction to its bonds. In fact, it is not believed that any glue has been developed which would completely eliminate the strap-separation problem.

While it is accordingly desirable to eliminate the fundamental causes of strap separation by constructing the straps from the same material as the bag, and making the straps as an integral part of the bag, attempts to do so have been unsuccessful. Latex bags are typically molded from liquid latex, and it has not been possible to produce bags having integral holding straps because of the limitations imposed by the molding process, such as the impracticality of designing molds having provisions for integral holding straps.

SUMMARY OF THE INVENTION

The invention herein includes both a method and apparatus for making a latex bag having integral holding straps or, in the alternative, an integral latex loop for accommodating a holding strap. In either case, the problem of strap separation is minimized because the strap (or loop) is formed from a material preferably having the same characteristics as the bag itself, and forms an integral part of the bag that cannot separate.

In addition, the present invention includes a latex bag having an integral loop or, in the alternative, integral holding straps As described in greater detail below, the method herein comprises the step of placing a portion of a latex strip on the surface of a latex bag while both the latex strip and latex bag portion are still in the process of curing. The strip and the bag portion are then permitted to cure while in contact with each other. To enhance the bond, a small quantity of wet, substantially uncured, latex can be added to the abutting surfaces prior to contact, thereby enhancing the integral bond thus formed. Since there is no material other than latex forming the bond, the resulting integral structure is not susceptible to separation owing to the substantially identical material characteristics throughout the thickness of the interfaced region. Accordingly, the continual deformation and resilient distortions of either the strap/loop or the bag is accommodated equally by all regions throughout the interfaced area.

Apparatus for carrying out the foregoing method is also disclosed herein, and comprises means for supporting the latex surface of the bag in a generally horizontal plane, and means for permitting a selected portion of a latex strip to contact the bag's surface, while retaining the non-contacting portions away from the bag during the curing time of the latex material thereof.

Finally, a novel product is disclosed herein comprising a latex container having at least one integrally formed latex loop or in the alternative, an integral holding strap.

Additional details concerning the invention will be apparent from the following description of the preferred embodiment, of which the drawings are a part.

DESCRIPTION OF THE PREFERRED EMBODIMENT

Figure 1:
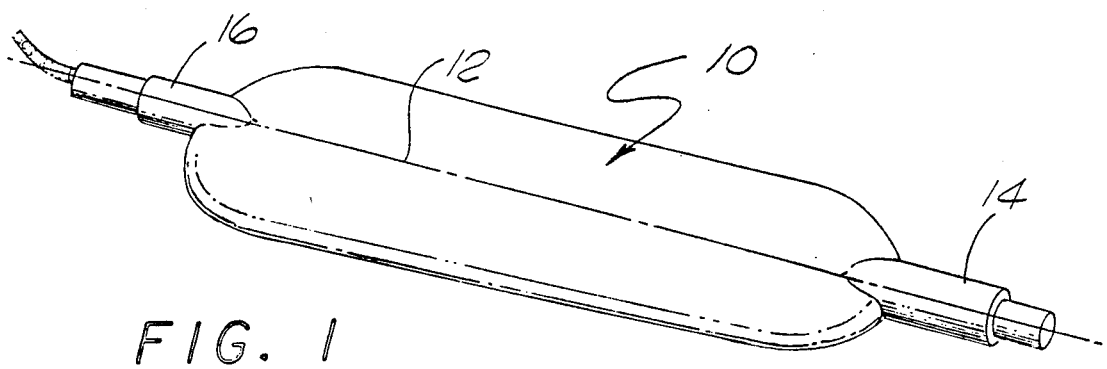
FIG. 1 is a perspective view of a prior art mold for making a latex bag.

FIG. 1 is a perspective view of a prior art mold utilized in the formation of a latex bag. The mold 10 has a paddle-like shape similar to the blade portion of an oar, and comprises a pair of axially extending, generally planar faces lying between a pair of oppositely-extending, generally cylindrical protrusions 14, 16 which extend axially at opposite ends of the mold.

In accordance with the invention, a pair of molds, such as that shown in FIG. 1, may conventionally be used to form the latex bag herein. One of the molds is used to form the bag itself, while the second mold is conveniently used in the formation of latex strips which are to be used as either hold straps or strap-accommodating loops on the bag. While the convenient use of the second identical mold will be appreciated from the following description, it should be noted that the strip-forming mold may be one of a number of shapes. It should also be recognized that there are a number of latex molding processes which can be used to form the bag and straps, and that the process used herein to mold these components has been chosen for convenience. Since these processes are well known, a complete description of the various reagents and materials is omitted for brevity.

In accordance with the invention, a pair of aluminum molds such as that illustrated in FIG. 1 are first cleaned, heated to 100° F. and dipped into a conventional alcohol coagulant solution containing calcium nitrate in the amount of 20% by weight. The molds are then air dried for three to four minutes.

The strip-forming mold is then dipped into a tank containing liquid latex in the form of a 51% solid latex mix. The bag-forming mold is dipped into a tank containing the same mix approximately five minutes after the strip-forming mold. Both of the molds are removed from the tanks approximately eight minutes after the bag-forming mold has been placed in the tank.

As is known to those skilled in the art, the latex adhering to the molds begins to cure from the inside out owing to the coagulant solution adhering to the mold surface. At room temperature, the liquid enters a gel phase but does not become sufficiently cross-linked to exhibit the resilient strength until vulcanization has taken place at a higher temperature. Typically, it takes approximately sixty minutes for the liquid latex to cure to a gel, and the remaining portion of the described process takes place within that curing period; preferably within the first 15–17 minutes.

Figure 2:
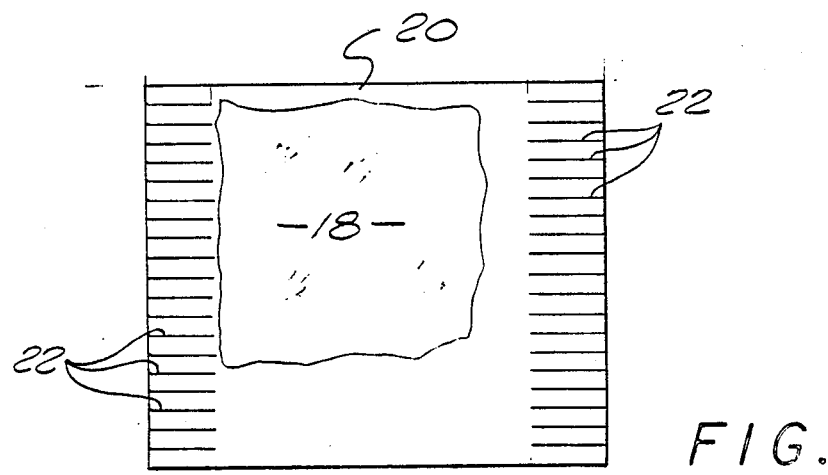
FIG. 2 is a top plan view illustrating a strip-forming technique and apparatus in accordance with the invention.

As soon as the molds are removed from the latex tanks, a sheet of latex approximately six inches by four inches is cut from the strip-forming mold. Referring to FIG. 2, the sheet 18 is placed, wet side up, on a piece of paper 20 having a plurality of parallel lines 22 on its opposing edges. The lines are approximately $\frac{3}{8}$ inch apart, and serve as indicia for the cutting of the latex sheet 18 into $\frac{3}{8}$ inch wide strips. Cutting is conveniently performed by a paper cutter, with the ends of each strip being trimmed to a desired length by means of an ordinary curved chisel. As will become evident from the following description, the paper strip underlying the curing latex serves as a backing, making it possible to handle and manipulate the curing strip of latex without leaving unacceptable marks or imperfections in the strip's appearance.

Figure 3:
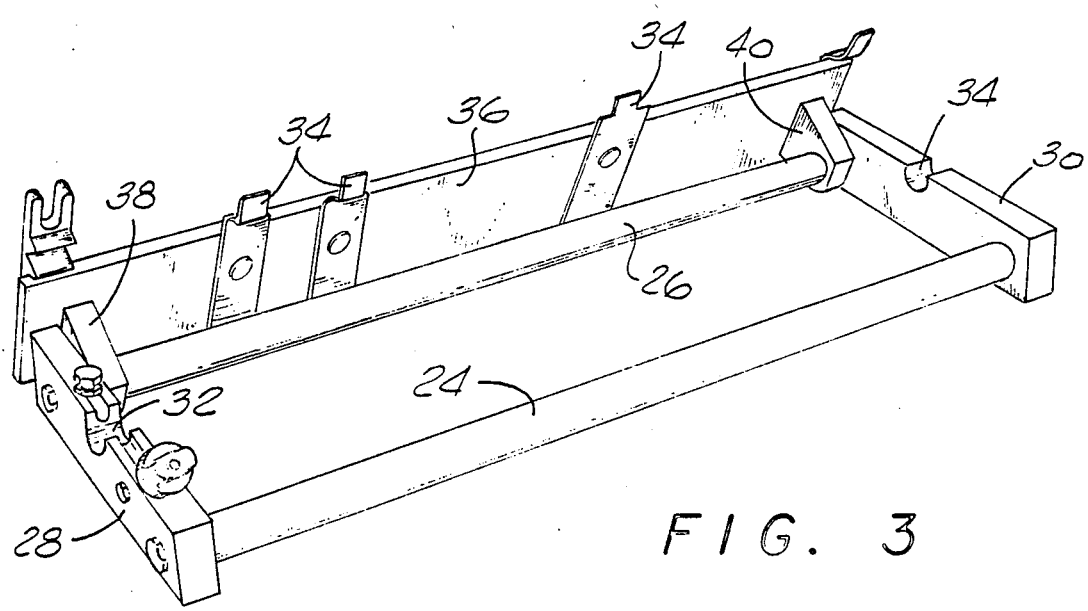
FIG. 3 is a perspective view illustrating a bag-accommodating apparatus constructed in accordance with the invention.
Figure 4:
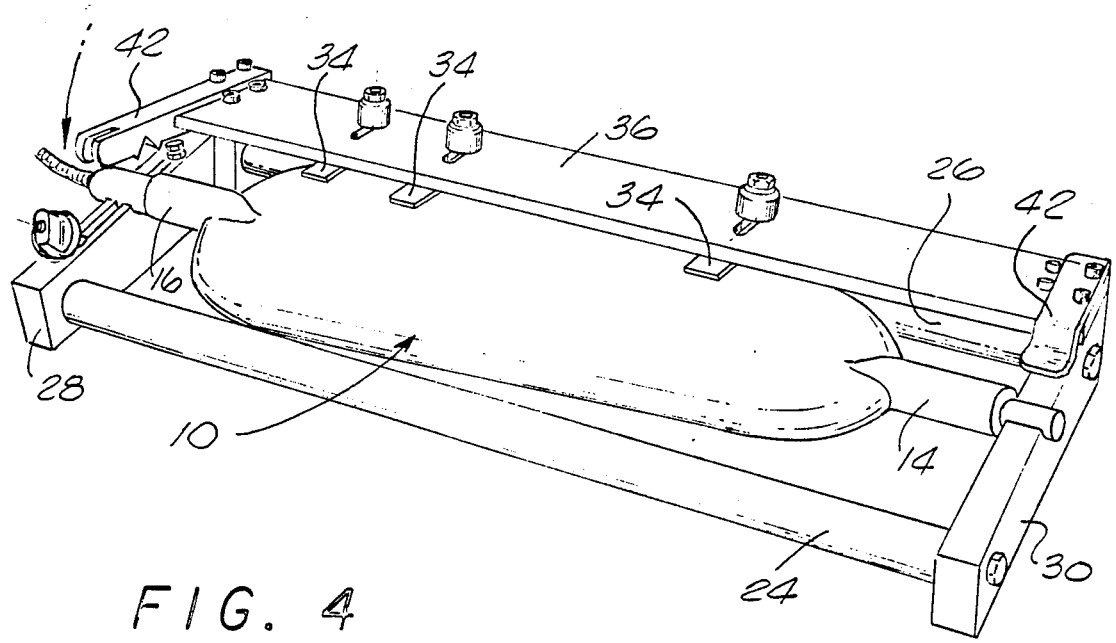
FIG. 4 is a perspective view of the apparatus in FIG. 3 accommodating a molded bag in accordance with the invention.
Figure 5:
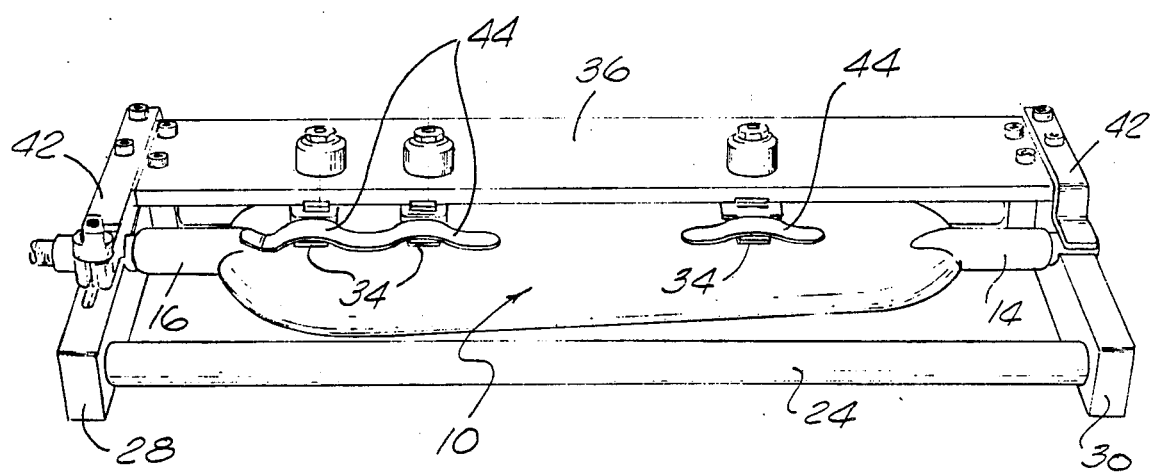
FIG. 5 is a perspective view of the apparatus shown in FIG. 4 showing the accommodation of latex loop-forming strips on the bag.

The bag-forming mold, is placed in an apparatus which is illustrated in perspective in FIGS. 3 and 4. Referring initially to FIG. 4, the apparatus is shown to comprise axially extending front and rear frame members 24, 26 which are fastened at their respective ends to left and right side frame members 28, 30. The side members 28, 30 include respective mold-receiving notches 32, 34 which are sized to accommodate the cylindrical extensions 16, 14 of the bag-forming mold, as best shown in FIG. 5. The apparatus further includes a plurality of finger-like extensions 34 of aluminum or Teflon (trademark for polytetrafluoroethylene) affixed to a member 36, which is mounted on the rear frame member 26 for rotation. The member 36 is coupled to the rear frame member 26 for rotation by a pair of transversely-extending lugs 38, 40.

As shown in FIG. 4, the latex-enclosed bag-forming mold is placed within the aforedescribed apparatus so that the cylindrical extensions 16, 14 are respectively captured within notches 32, 34 of the left and right frame members 28, 30. The member 36 is then rotated about the rear frame member 26 so that the fingers 34 extend generally forward over the upper surface of the bag-forming mold, approximately $\frac{1}{4}$-inch above the latex surface. It may be noted that the member 36 conveniently includes a finger-like tab 42 at each of its ends dimensioned and positioned to overlie the notches 32, 34 (FIG. 4) when the fingers 34 are overlying the bag. The tabs 42 capture the cylindrical extensions 16, 14 of the mold within the notches.

As best illustrated in FIG. 5, the strips 44 which were cut from the sheet 18 (FIG. 2) are next placed on the latex surface of the bag while both the strips and bag are curing. In FIG. 5, the strips are arranged to form loops on the bag, through which holding straps are to be placed. Accordingly, the fingers 34 are adapted to hold the central portion of the strips away from the curing latex surface of the bag as both the strips and the bag continue to cure.

Before the strips are positioned over the fingers 34, it is preferable to place approximately five drops of wet latex on the areas of the bag which will interface with the curing latex of the strips. The strips 44, handled by their underlying paper backing, are placed over the latex surface of the bag, inverted so that the paper backing faces upwardly, and positioned over a respective tab 34 so that the ends of the strip 44 are in contact with the curing latex surface of the bag. The ends of the strips are then pushed lightly against the bag until the interfacing surfaces adhere to each other. The paper backing is subsequently, and conveniently, pealed from the strip after the strip has been sealed to the bag.

The bag and attached strips are then permitted to air dry at 75° F. for approximately twenty minutes, and are then leached in soft water at 120° F. for sixty minutes. Following the leaching process, the bag and apparatus are heated for approximately eight hours at 150° F. The bag is then removed from the mold, soaped to lubricate its stripping from the mold, and stripped from the mold.

The final product is a latex bag having integral loops. The interfacing surfaces of the bag and loops form an integral bond, with no material other than latex being involved.

While the foregoing is a description of the preferred embodiment, it is recognized that there are numerous modifications and variations which can be made to the described apparatus and method without departing from the spirit of the invention. For example, a long strip may be used to contact the bag at both its ends and at its mid-portion, forming a double loop as shown at the left end of the bag illustrated in FIG. 5. Additionally, a latex strip may, itself, be employed as a holding strap by orienting it approximately perpendicular to the bag's axis and joining its mid-portion to the bag.

Naturally, methods other than that disclosed above for forming the latex strips will be equally suitable. For example, a "cookie cutter" approach may be used, wherein a die cuts the strip from the latex sheet.

It is also possible that objects may be placed on the curing latex surface of the bag to hold the non-adhering portions of the strips away from the bag's surface while the latex cures. For example, small, square-shaped pieces of plastic have been used but have left unacceptable marks on the face of the bag.

It should accordingly be recognized that the description of the preferred embodiment is only illustrative in nature and that modifications and variations will be apparent to those skilled in the art having the benefit of these teachings. It is accordingly intended that the invention herein be defined solely by the claims appended hereto and that the claims be interpreted as broadly as permitted in light of the prior art.

I claim:

1. Apparatus for forming an integral latex loop on a latex rubber surface comprising in combination:

first and second portable molds configured to be dipped into a container of liquid latex and for respectively supporting first and second curing latex surfaces formed thereon after removal from the container;

a frame member for releasably securing said first portable mold so that said first curing latex surface thereon is oriented in a generally horizontal plane;

a cuttable substrate for supporting the second latex surface subsequent to removal of said second latex surface from said second mold;

cutting means for cutting the substrate and said second latex surface thereon into a plurality of generally strip-shaped lengths of latex and substrate, each length having a pair of end portions separated by a mid-portion; and means for supporting the mid-portion of a said strip-shaped length of latex and substrate above said first latex surface sufficiently close to permit the latex at the end portions of said strip-shaped length to contact said first latex surface for integral bonding therewith as the latex surfaces continue to cure to form an integral loop on said first latex surface, the substrate being removable from the strip-shaped length after the latex surfaces have bonded.

2. The apparatus of claim 1 wherein the supporting means includes a tab-like protrusion extending over said first latex surface at a predetermined distance therefrom which enables the end portions of a strip-shaped length to contact said first latex surface, and said protrusion having an upper receiving surface for retaining the mid-portion of the strip-shaped length away from said first latex surface in a loop-forming orientation.

3. The apparatus of claim 1 wherein the substrate is made of a disposable material.

4. The apparatus of claim 3 wherein the substrate is made of paper.

5. The apparatus of claim 1 wherein the substrate includes indicia for visually demarking the location of strip-forming cuts to be made by the cutting means.

* * * * *